United States Patent [19]
Ito

[11] Patent Number: 5,993,381
[45] Date of Patent: Nov. 30, 1999

[54] OPERATING UNIT FOR AN ENDOSCOPE

[75] Inventor: Keiji Ito, Saitama, Japan

[73] Assignee: Asahi Kogaku Kogyo Kabushiki Kaisha, Tokyo, Japan

[21] Appl. No.: 09/135,838

[22] Filed: Aug. 18, 1998

[30] Foreign Application Priority Data

Aug. 18, 1997 [JP] Japan .................................. 9-221279

[51] Int. Cl.⁶ .................................................. A61B 1/005
[52] U.S. Cl. ......................... 600/131; 600/167; 600/146
[58] Field of Search .................................. 600/131, 132, 600/112, 106, 146, 147, 148, 149, 163, 167, 168, 174, 175

[56] References Cited

U.S. PATENT DOCUMENTS

| | | | |
|---|---|---|---|
| 4,777,524 | 10/1988 | Nakajima | 600/167 |
| 4,832,473 | 5/1989 | Ueda | 600/167 |
| 4,905,082 | 2/1990 | Nishigaki | 600/109 |
| 4,969,450 | 11/1990 | Chinnock | 600/163 |
| 4,991,957 | 2/1991 | Sakamoto | 385/118 |
| 5,305,736 | 4/1994 | Ito . | |
| 5,341,240 | 8/1994 | Boome | 600/163 |
| 5,411,020 | 5/1995 | Ito | 600/146 |
| 5,667,476 | 9/1997 | Frassica | 600/146 |
| 5,702,349 | 12/1997 | Morizumi | 600/167 |
| 5,733,245 | 3/1998 | Kawano | 600/146 |
| 5,735,794 | 4/1998 | Koeda et al. . | |
| 5,842,972 | 12/1998 | Wulfsberg | 600/167 |

FOREIGN PATENT DOCUMENTS

| | | |
|---|---|---|
| 49-13034 | 3/1974 | Japan . |
| 63-47320 | 3/1988 | Japan . |
| 63-269113 | 11/1988 | Japan . |

*Primary Examiner*—John P. Leubecker
*Attorney, Agent, or Firm*—Greenblum & Berstein, P.L.C.

[57] ABSTRACT

An operating unit for an endoscope is provided in which focusing and/or zooming operations can be easily performed using a hand holding an operating unit, without removing a hand holding an insertion unit from the insertion unit. An optical system operating member for performing focusing and/or zooming operations on an observation optical system is disposed at a position where the optical system operating member is operable by the thumb of a hand holding an operating unit. The optical system operating member is arranged to be coaxially rotatable with a bending operation member disposed on a side face of the operating unit.

6 Claims, 11 Drawing Sheets

PROXIMITY MAGNIFICATION OBSERVATION

OPERATING UNIT FOR AN ENDOSCOPE

BACKGROUND OF THE INVENTION

1. Field of the Invention

The present invention relates to an operating unit for an endoscope having focusing and/or zooming functions.

2. Description of the Related Art

Japanese Patent Kokai Publication No. 63-269113 discloses an operating unit for an endoscope having focusing and/or zooming functions. The endoscope has an objective optical system forming an image on an image receiving unit of an image transmitting system. The objective optical system and the image receiving unit are both installed in a front end of an insertion unit of the endoscope. To remotely control a relative distance between the objective optical system and the image receiving unit for focussing and/or zooming, the operating unit is equipped with an optical system operating ring 79 for moving one or both of the objective optical system and the image receiving unit back and forth through an operating wire passing through the insertion unit. The optical system operating ring 79 is provided on an eyepiece projecting from the head portion of the operating unit and is juxtaposed to a diopter adjusting ring 121.

The operating ring 79 provided on the eyepiece is located at a position where the fingers of the left hand holding the operating unit cannot reach. Therefore, the operating ring 79 must be operated using the right hand.

In contrast to the diopter adjustment ring 121, which need not be adjusted during endoscopic observation after it has been initially adjusted, the optical system operating ring 79 for performing focusing and/or zooming operations must be operated at a most critical time when the objective diseased part is observed through the endoscope. If the optical system operating ring is operated at this time using the right hand, which must be used for holding the insertion unit, the front end of the insertion unit is unintentionally moved from a position where the objective diseased part can be observed. Consequently, a series of operations, starting with an operation of guiding the front end of the insertion unit to the objective diseased part, must be repeated.

SUMMARY OF THE INVENTION

Therefore, it is an object of the present invention to provide an operating unit for an endoscope in which focusing and/or zooming operations can be easily performed using a hand holding an operating unit, without removing the hand holding an insertion unit from the insertion unit.

In order to attain this object, the operating unit for an endoscope of the present invention is characterized in that an optical system operating member for performing focusing and/or zooming operations on an observation optical system is disposed at a position where the optical system operating member is operable by a thumb of a hand holding the operating unit.

A bending unit is formed at a tip end portion of an insertion unit. A bending operation knob for remotely bending the bending unit may be disposed on a side face of the operating unit. The optical system operating member may be coaxially rotatable with the bending operation knob.

The optical system operating member may be disposed between a side face of the operating unit and the bending operation knob, while being directed toward an operator holding the operating unit.

According to the present invention, the optical system operating member for performing focusing and/or zooming operations on the observation optical system is disposed at a position where the optical system operating member is operable by a thumb of a hand holding the operating unit. Therefore, the focusing and/or zooming operations can be easily performed using the hand holding the operating unit, while not removing the hand holding the insertion unit from the insertion unit. As a result, an observation image at an optimum magnification can be easily obtained.

The present disclosure relates to the subject matter contained in Japanese patent application No. Hei. 9-221279 (filed on Aug. 18, 1997) which is expressly incorporated herein by reference in its entirety.

DETAILED DESCRIPTION OF THE PREFERRED EMBODIMENT

Figure 1:
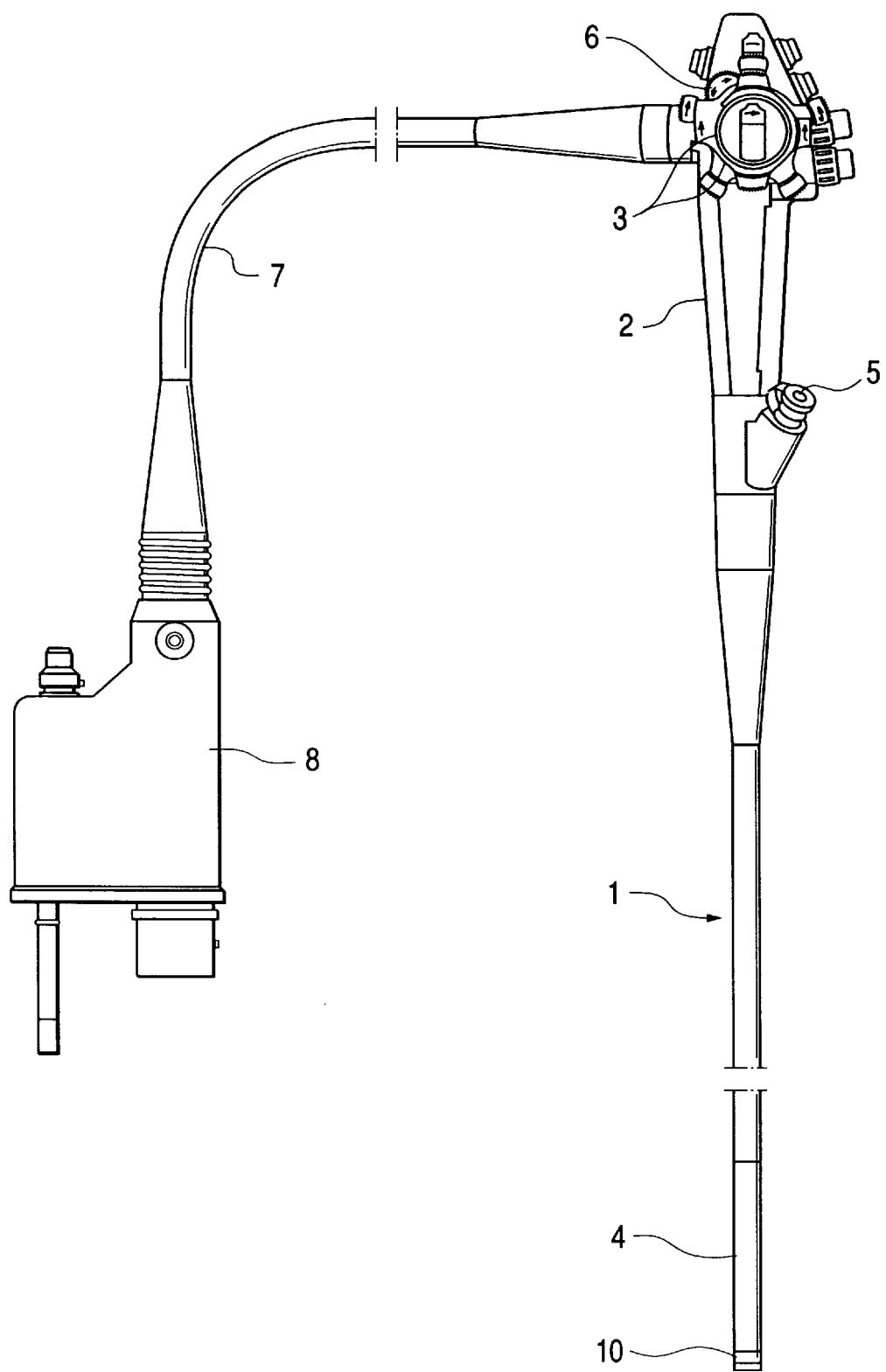
FIG. 1 is a side view showing an entire configuration of an endoscope.

FIG. 1 shows the entire configuration of an endoscope. An operating unit 2 is coupled to the rear end of a flexible pipe-like insertion unit 1. A bending unit 4 at a front end portion of the insertion unit 1 can be bent in any direction at an arbitrary angle by rotating a bending operation knob 3 which projects from a side face of the operating unit 2.

A front end main body 10, in which an object optical system and the like are incorporated, is coupled to the front end portion of the bending unit 4. A treatment tool insertion port 5 (i.e., an inlet of a treatment tool insertion channel passing through the insertion unit 1) is provided adjacent to a portion where the insertion unit 1 and the operating unit 2 are coupled together.

Reference numeral 6 designates an optical system operating lever (i.e., an optical system operating member) which is used for performing focusing and zooming operations, and which is rotatable coaxially with respect to the bending operation knob 3. The optical system operating lever 6 is disposed between the side face of the operating unit 2 and the bending operation knob 3, with the distal end of the operating lever 6 facing the operator holding the operating unit 2.

A connector 8 is coupled to a front end of a flexible coupling tube 7, which is coupled to the rear portion of the operating unit 2. The connector 8 is connected to a combined device (not shown) serving as a light source and a video processor. The combined device supplies illumination light to an illumination light guide fiber bundle (described later), and performs processing such as a processing of a video signal generated by a solid state imaging device incorporated in the front end main body 10.

Figure 3:
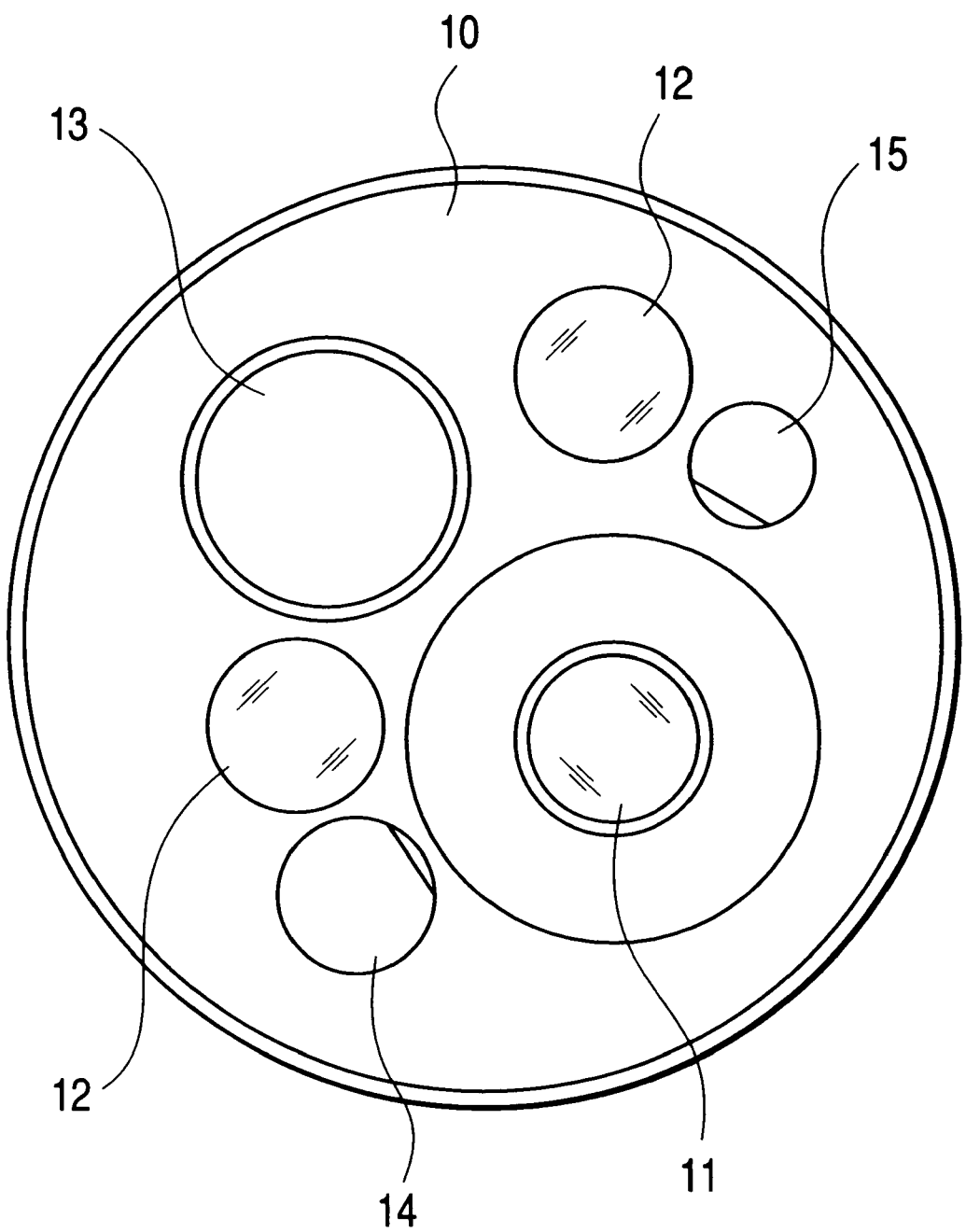
FIG. 3 is a front view of a front end of an insertion unit of the endoscope.

FIG. 3 is a front view of the front end main body 10. The reference numeral 11 designates an observation window through which an observation image is to be taken, 12 designates a pair of illumination windows through which illumination light for illuminating an object to be observed is emitted, 13 designates an outlet of the treatment tool insertion channel, and 14 and 15 designate an air supply nozzle and a water supply nozzle, respectively.

Figure 4:
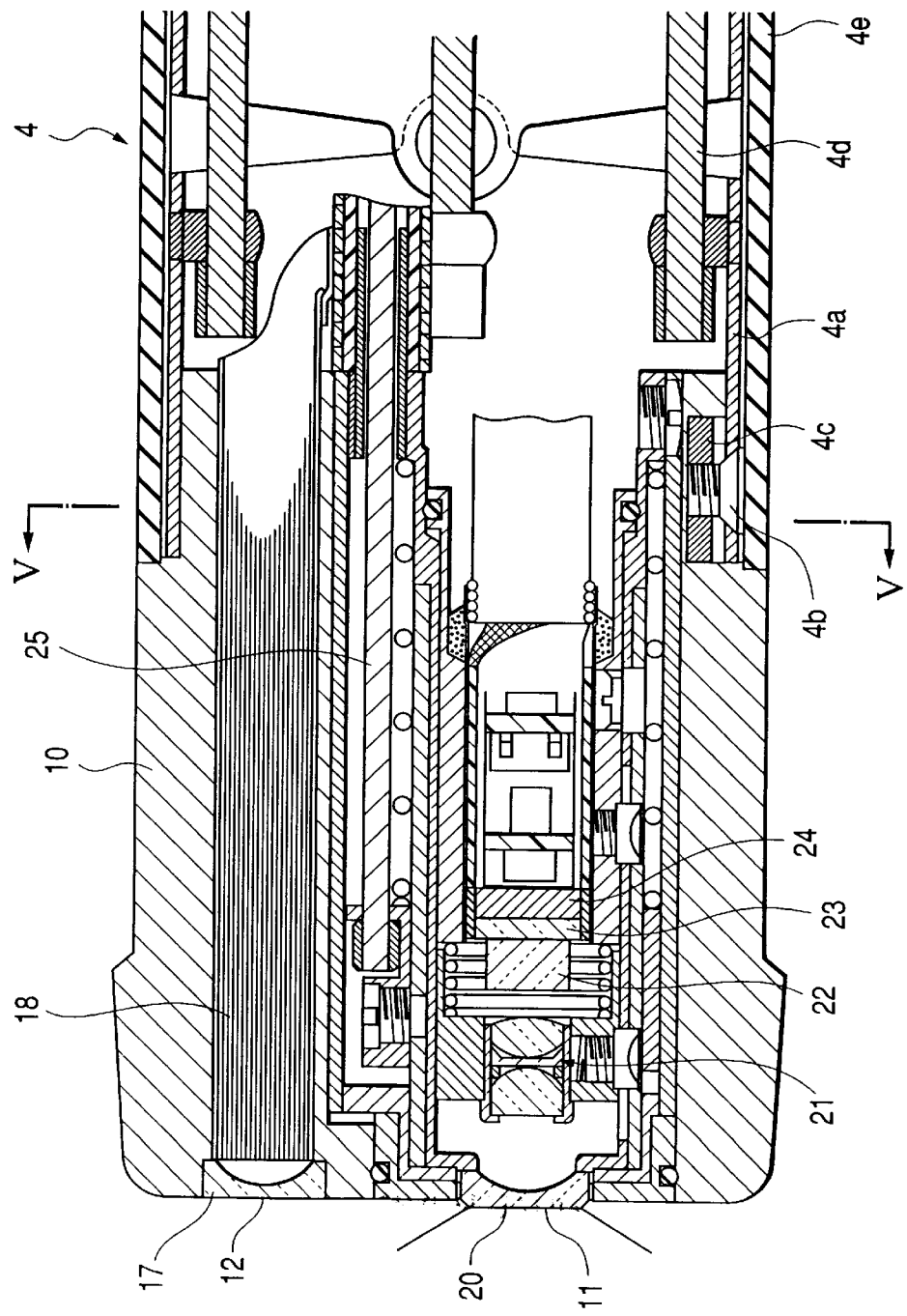
FIG. 4 is a side section view of the front end of the insertion unit of the endoscope.
Figure 5:
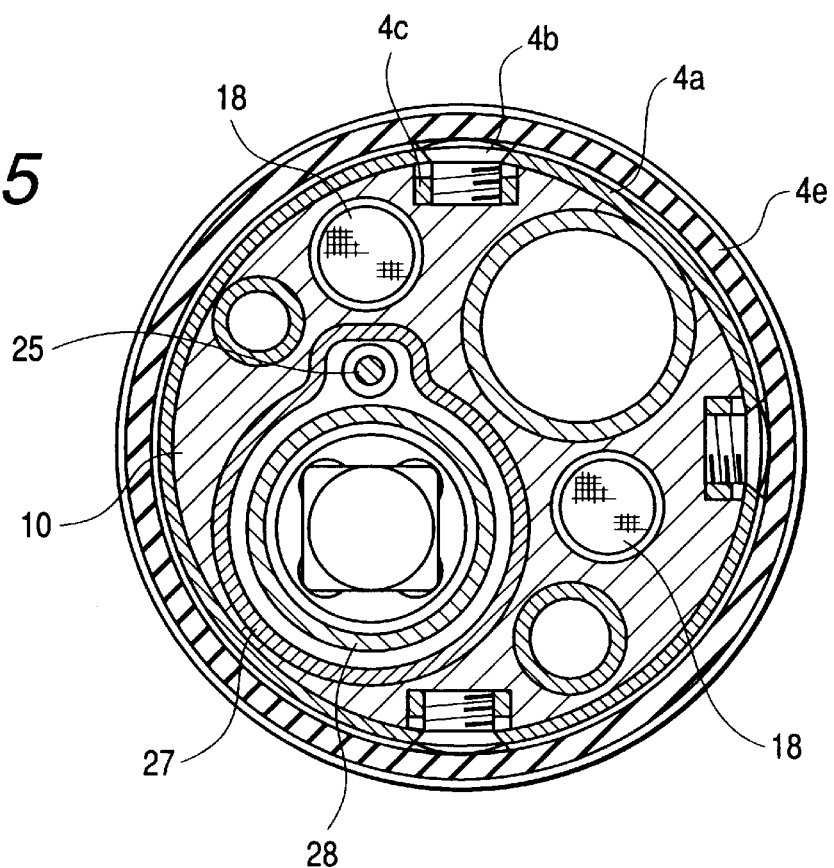
FIG. 5 is a section view taken along a line V—V of FIG. 4.

FIG. 4 is a side section view of the front end portion of the insertion unit 1, taken along a plane containing the center lines of the observation window 11 and one illumination window 12, and FIG. 5 is a section view taken along a line V—V of FIG. 4. The reference numerals 4 and 10 designate the bending unit and the front end main body, respectively.

A concave lens 17, which increases the distribution angle of the illumination light, is fitted into the illumination window 12. The emission end of the illumination light guide fiber bundle 18 is disposed inside the illumination window 12. A cover lens 20 serving as a first lens of the objective optical system is fitted into the observation window 11. Disposed inside the observation window 11, are an objective lens group 21 of the objective optical system, the solid state imaging device 24, etc. Reference numeral 22 designates a YAG laser cut filter, and 23 designates a cover glass.

The framework of the bending unit 4 is configured by plural joint rings rotatably coupled to one another with rivets. The foremost joint ring 4a is fitted onto the outer peripheral face of the rear end portion of the front end main body 10, and fixedly coupled thereto by a fixing screw 4b.

Reference numeral 4c is a screw block disposed in a recess formed in the front end main body 10, to which the fixing screw 4b is screwed. Reference numeral 4d designates a bending operating wire, and 4e designates an elastic rubber sheath tube.

Figure 2:
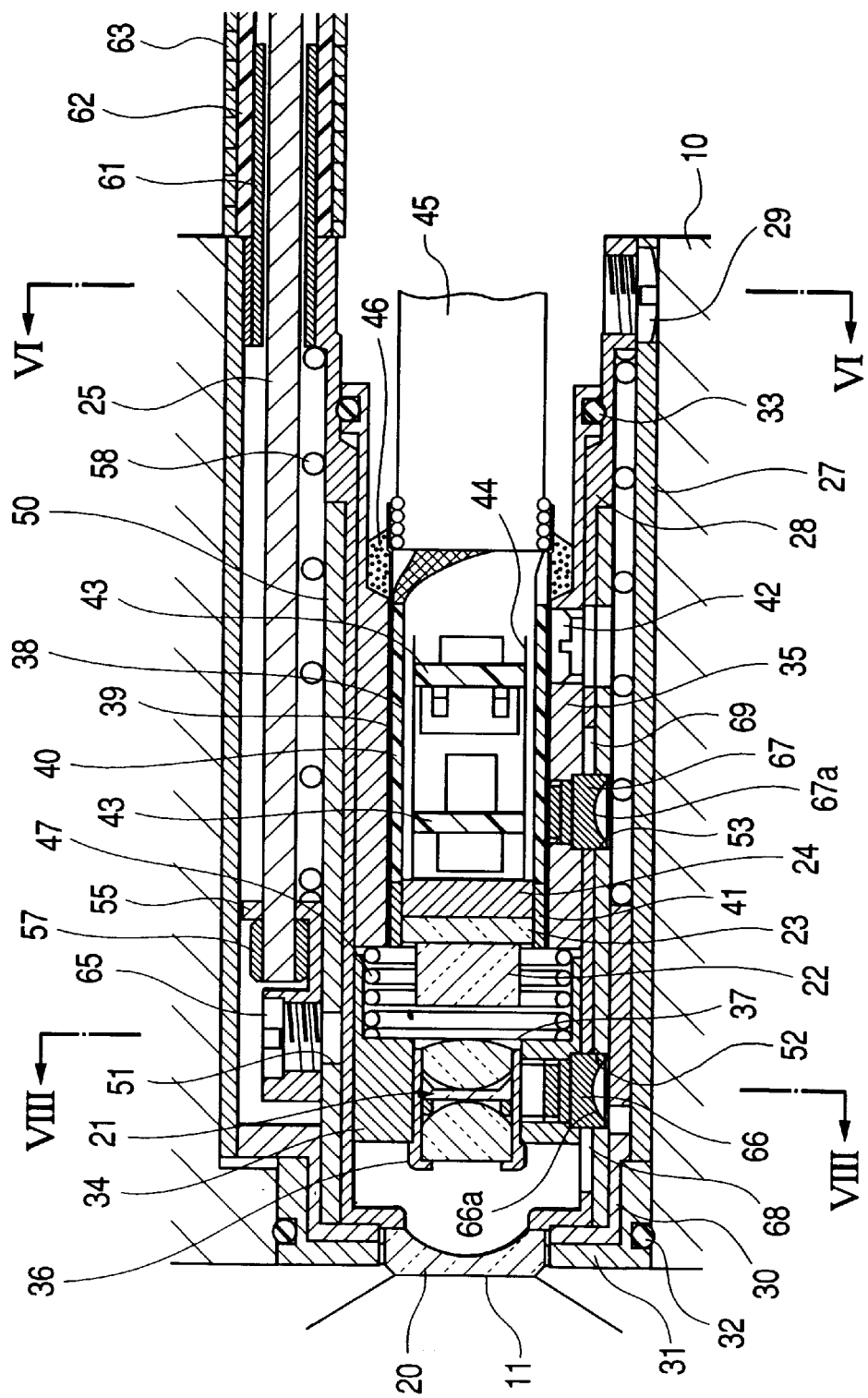
FIG. 2 is an enlarged side section view mainly showing an objective optical system under a normal observation state.
Figure 6:
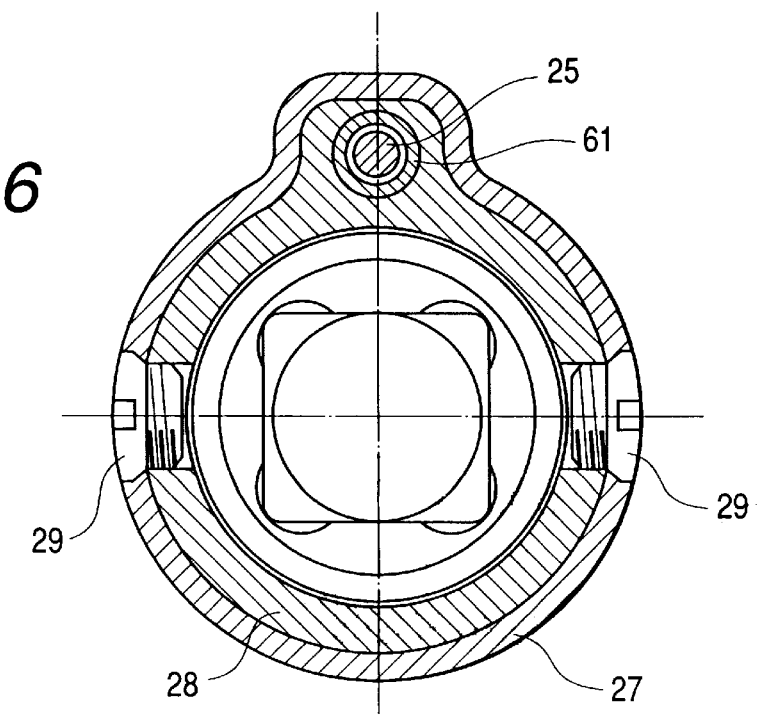
FIG. 6 is a section view taken along a line VI—VI of FIG. 2.
Figure 8:
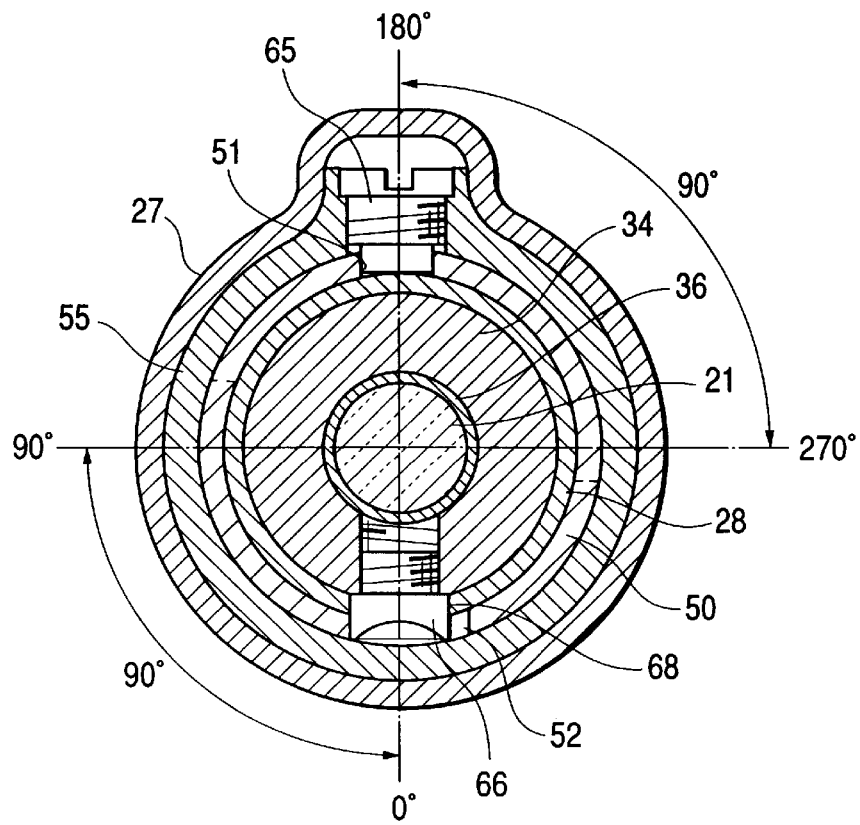
FIG. 8 is a section view taken along a line VIII—VIII of FIG. 2.

FIG. 2 is an enlarged view showing the peripheral structure surrounding the objective optical system 20, 21 and the solid state imaging device 24 under a normal observation state. FIGS. 6 and 8 are section views taken along lines VI—VI and VIII—VIII of FIG. 2, respectively.

A stationary outer tube 27 is fittingly inserted and fixed into a hole that extends through the front end main body 10 in the axial direction. The rear portion of a stationary inner tube 28 is directly fitted to the stationary outer tube 27, and fixed thereto by fixing screws 29 (see FIG. 6). On the front portion of the stationary inner tube 28, a space ring 30 is provided so that the space ring 30 is radially interposed between the tubes 27 and 28. With this arrangement, a predetermined clearance is ensured between the tubes 27 and 28, with the exception of the front and rear portions thereof.

The cover lens 20 is fixed to the front end of the stationary inner tube 28 in a water-tight manner by caulking. A front cover 31 is overlaid on the space ring 30 so as to close a gap between the side face of the cover lens 20 and the front end main body 10.

An interface between the front cover 31 and the side face of the cover lens 20 is filled with a degassed epoxy adhesive agent. A seal O-ring 32 is provided between the fitting faces of the front cover 31 and the front end main body 10.

An objective lens frame 34 to which the objective lens group 21 is attached, and an imaging unit frame 35 to which the solid state imaging device 24 for taking an observation image is attached, are inserted and fitted into the stationary inner tube 28, so that they move forwardly and rearwardly in the axial direction independently from each other. Reference numeral 33 designates an O-ring.

The objective lens group 21 is incorporated into a lens tube 36 and fixed thereto by caulking. The lens tube 36 is fixedly coupled to the objective lens frame 34. The lens tube 36 may be fixed to the objective lens frame 34 using screws.

Reference numeral 37 designates a light shielding mask that removes unnecessary marginal rays. An aperture diaphragm (not shown) is disposed at the front end face of the objective lens group 21. A first compression coil spring 47 is interposed between the frames 34 and 35 so as to urge the objective lens frame 34 and the imaging unit frame 35 away from each other, thereby preventing rattling thereof.

The solid state imaging device 24 is fixed to the front end of a flexible board 44 such as a TAB (Tape Automated Bonding) board. The cover glass 23 is attached to the front end face of the solid state imaging device 24, and the YAG laser cut filter 22 is attached to the front end face of the cover glass 23. An endoscopic observation image, which is formed by the objective optical system 20 and 21, is converted into electrical signals by the solid state imaging device 24.

Disposed inside the flexible board 44, is a pair of buffer boards 43 on which electronic parts constituting circuits such as a driving circuit for the solid state imaging device 24 are mounted. A signal cable 45 is rearwardly drawn out from the flexible board 44.

An electrically insulative thin tape 38 is continuously wound around the outer peripheral faces of the cover glass 23, the solid state imaging device 24, and the flexible board 44. An electrically conductive shield cylinder 40 is fitted on the electrically insulative thin tape 38, and a shield wire of the signal cable 45 is connected to the shield cylinder 40.

The front end of the shield cylinder 40 is located at an axially intermediate position on the side face of the solid state imaging device 24. Therefore, the space extending from that position to the front end of the cover glass 23 is filled with a degassed electrically insulative epoxy adhesive agent 41, which covers the outer face portion of the insulating tape 38.

Another insulative tape 39 is continuously wound around the outer peripheries of the insulative epoxy adhesive agent 41 and the shield cylinder 40 so as to ensure the electrical insulation between the shield cylinder 40 and the imaging unit frame 35. Reference numeral 46 designates a silicone adhesive agent that is filled into the rear end side of the imaging unit frame 35 in order to prevent dust from entering the imaging unit frame 35.

The shield cylinder 40, which houses the solid state imaging device 24 and the electronic circuits, is fixed to the imaging unit frame 35 by the pressure of a fixing screw 42 screwed into the imaging unit frame 35. To perform the focus-setting operation under the normal observation state, the fixing screw 42 is loosened once and the focus is then checked while the mode is switched to a proximity magnification observation state (to be described later). When the focus is satisfactory, the screw is fastened to fix the shield cylinder 40 to the imaging unit frame 35.

Since the electrical insulating tape 39 is interposed between the end face of the fixing screw 42 and the outer peripheral face of the shield cylinder 40, the electrical insulation between the imaging unit frame 35 and the shield cylinder 40 is ensured.

A cam cylinder 50, on which first, second, and third cam grooves 51, 52, and 53 are formed, is fitted onto the outer peripheral face of the stationary inner tube 28, so as to be rotatable about the axis. A slide cylinder 55 that is driven to slide in the axial direction by an operating wire 25 is disposed so as to surround the cam cylinder 50.

The front end of the operating wire 25 is passed through a hole formed in the slide cylinder 55. A lock ring 57 is fixed to the front end of the operating wire. The slide cylinder 55 is slidingly driven in the rightward direction in FIG. 2 by pulling the operating wire 25 with the optical system operating lever 6 on the operating unit 2.

When the operating wire 25 is moved in the opposite direction (i.e., the forward direction), the slide cylinder 55 is slidingly driven in the leftward direction in FIG. 2 by the urging force of a second compression coil spring 58. This second compression coil spring 58 is disposed so as to surround the outer periphery of the stationary inner tube 28. The urging force of the second compression coil spring 58 is set to be greater than that of the first compression coil spring 47 under the normal observation state.

Reference numerals 62 and 63 cooperatively designate a guide pipe, which has a double structure and guides the operating wire 25 in the insertion unit 1. The inner side of the guide pipe is a flexible tube 62, and the outer side thereof is a pipe 63 made of a closely wound coil having a rectangular section shape. The guide pipe is adhesively fixed to a connecting pipe 61, which is soldered to the stationary outer tube 27. The flexible tube 62 prevents an applied lubricant from entering various incorporated members of the insertion unit 1.

A first pin 65 is fixedly screwed into the slide cylinder 55 so as to project inwardly therefrom. The end of the first pin movably engages with the first cam groove 51 formed in the cam cylinder 50.

A second pin 66 is fixedly screwed into the objective frame 34 so as to project outwardly therefrom. The head portion of the second pin engages with the second cam groove 52. A third pin 67 is fixedly screwed into the imaging unit frame 35 so as to project outwardly therefrom. The head portion of the third pin engages with the third cam groove 53.

Figure 9:
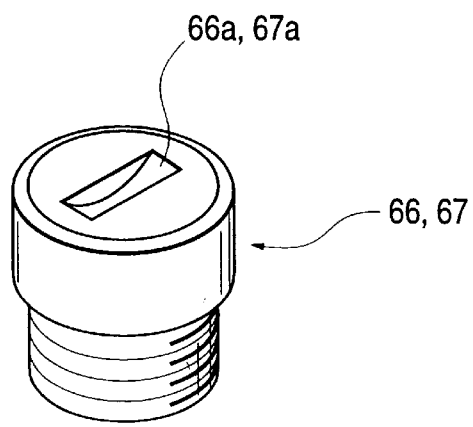
FIG. 9 is a perspective view of a pin.

Rectilinear grooves 68 and 69, through which the second and third pins 66 and 67 pass, are formed in the stationary inner tube 28 in the axial direction. Since the head portions of the second and third pins 66 and 67 engage with the second and third cam grooves 52 and 53, respectively, the outer peripheral surfaces of the head portions of the second and third pins 66 and 67 are made smooth, as shown in FIG. 9. That is to say, each of slotted grooves 66a and 67a with which a screw driver is to be engaged during an assembly process is provided in a form of crescent-like recess that is not continuous to the outer peripheral surface of the head portion of the pin 66 (67), as shown also in FIG. 9.

Figure 7:
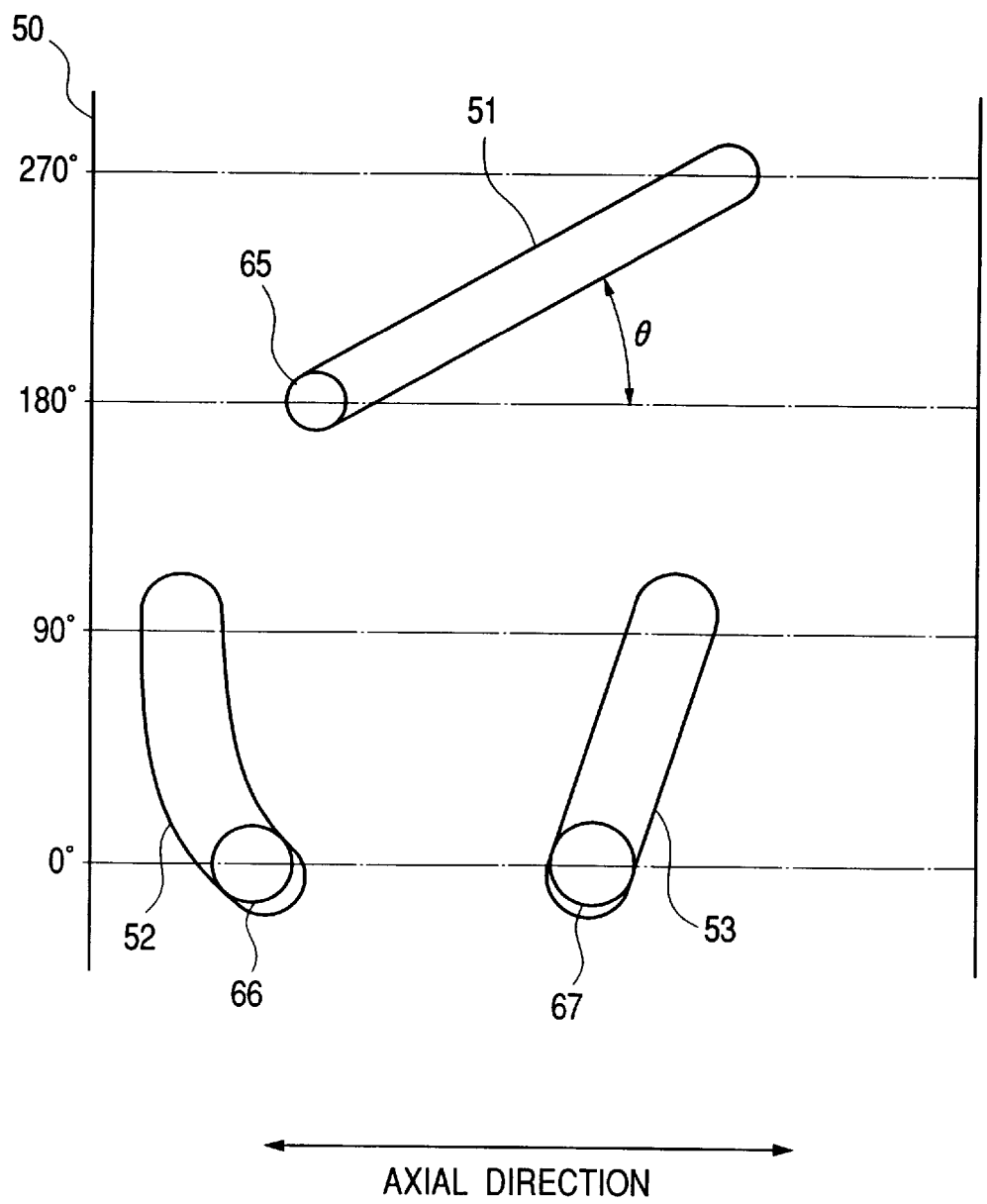
FIG. 7 is a development view showing engagement states between cam grooves and pins under the normal observation state.

FIG. 7 is a development view showing engagement states between the first to third cam grooves 51 to 53 and the first to third pins 65 to 67. In FIG. 7, the pins 65, 66, and 67 are located at positions of the normal observation state shown in FIGS. 2 and 8, etc.

Preferably, an angle θ of the first cam groove 51 with respect to the axial direction of the cam cylinder 50 (i.e., the optical axis direction) is in the range of 10° to 45°, so as to smoothly perform operations using a small operating force. In the embodiment, the angle is set to be θ≈30°.

Under this normal observation state, if the optical system operating lever 6 of the operating unit 2 is operated to pull the operating wire 25 toward the operating unit 2, the slide cylinder 55 slides against the urging force of the second compression coil spring 58 in the rearward direction (i.e., the rightward direction), and the first pin 65 (which is moved together with the slide cylinder 55 while being kept in engagement with the first cam groove 51) rotates the cam cylinder 50 about the axis. See FIG. 10. The rotation angle is 90° at the maximum.

When the cam cylinder 50 is rotated about the axis, the second and third pins 66 and 67 kept in engagement with the second and third cam grooves 52 and 53 formed in the cam cylinder 50 are moved in the axial direction. As a result, the objective lens frame 34 slides in the forward direction (i.e., the leftward direction in FIG. 10) and the imaging unit frame 35 slides in the rearward direction (i.e., the rightward direction in FIG. 10).

The length of the first cam groove 51 is set so as to rotate the cam cylinder 50 at just 90°, whereas each of the second and third cam grooves 52 and 53 is longer in length than the first cam groove 51. Therefore, the first cam groove 51 and the first pin 65 engaged therewith serve as a stopper for regulating the maximum rotation angle of the cam cylinder 50.

Figure 10:
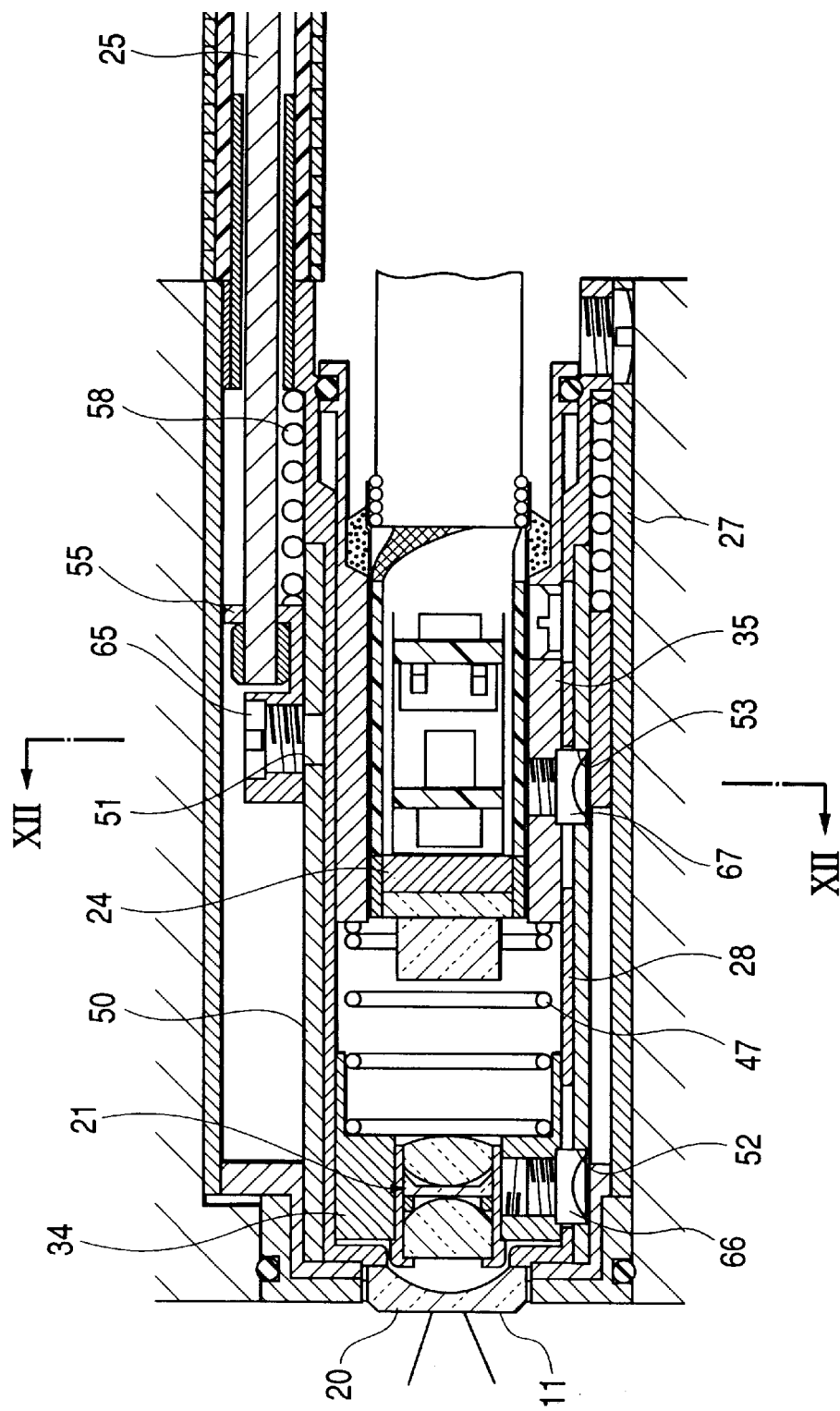
FIG. 10 is an enlarged side section view mainly showing the objective optical system under a proximity magnification observation state.
Figure 11:
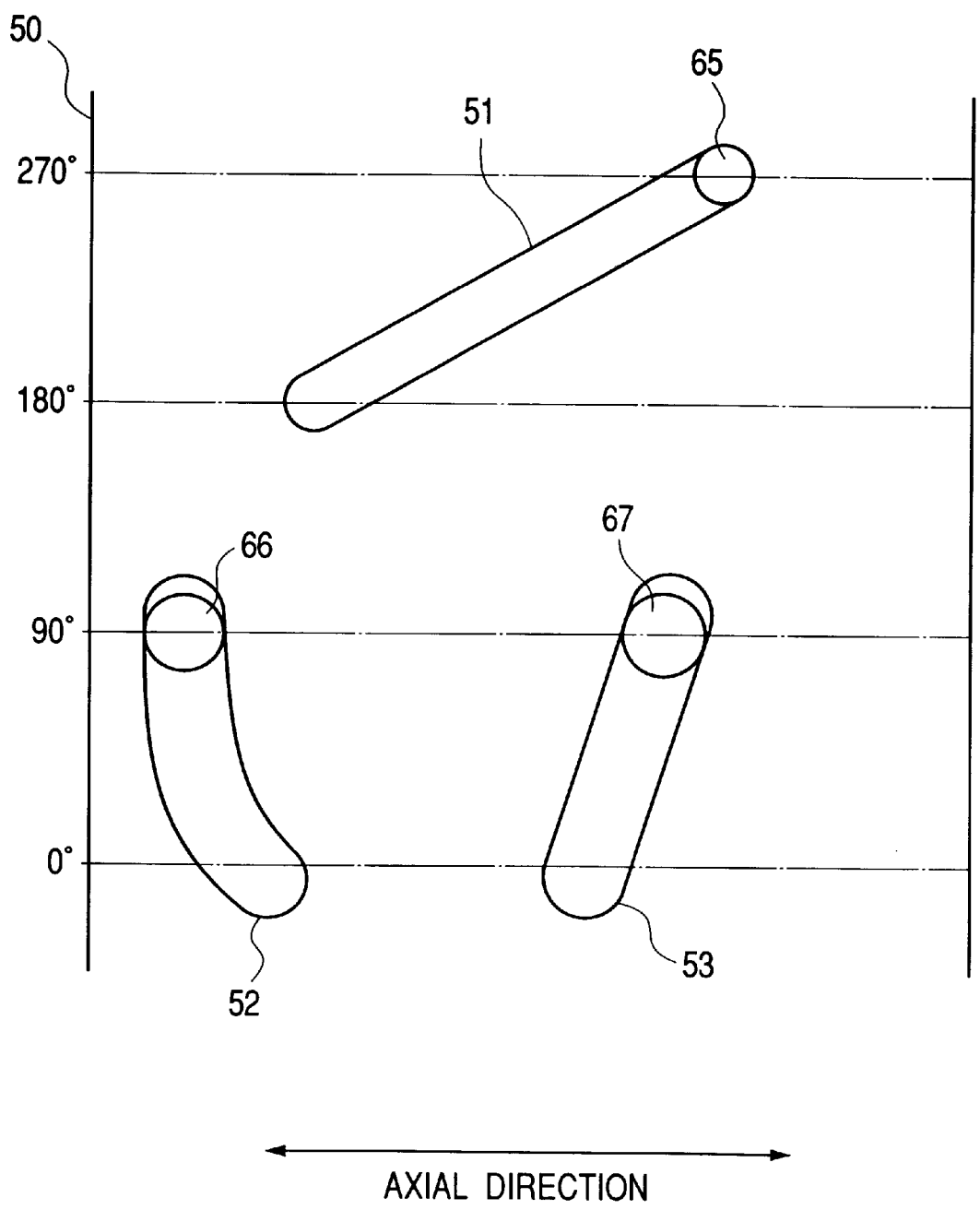
FIG. 11 is a development view showing engagement states between the cam grooves and the pins under the proximity magnification observation state.
Figure 12:
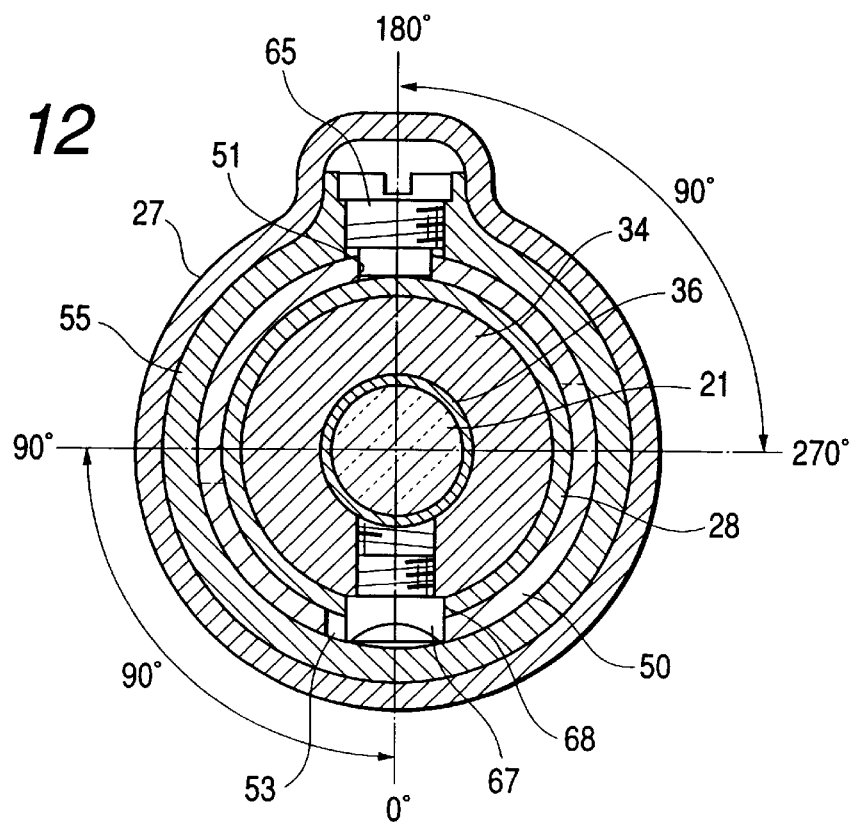
FIG. 12 is a section view taken along a line XII—XII of FIG. 10.

FIG. 11 is a development view showing engagement states between the first to third cam grooves 51 to 53 and the first to third pins 65 to 67 under a state where the cam cylinder 50 has been rotated by 90°. FIG. 12 is a section view taken along a line XII—XII in FIG. 10.

In the state shown in FIGS. 10 to 12, the objective lens group 21 has been forwardly moved and the solid state imaging device 24 has been rearwardly moved while the cover lens 20 is kept stationary. As a result, the focusing and zooming operations are simultaneously performed so that, for example, the normal observation state in which the angle of field is 120° and the observation distance is 5 to 100 mm is changed to a microscopic proximity magnification observation state in which the angle of field is 40° and the observation distance is 2 to 4 mm.

If the operation of the optical system operating lever 6 is stopped at an arbitrary intermediate position, the objective lens frame 34 and the imaging unit frame 35, which are driven via the operating wire 25 and the slide cylinder 55, are stopped at intermediate positions in their moving ranges. This allows the observation to be performed at an arbitrary magnification that is between the normal observation state and the proximity magnification observation state.

Figure 13:
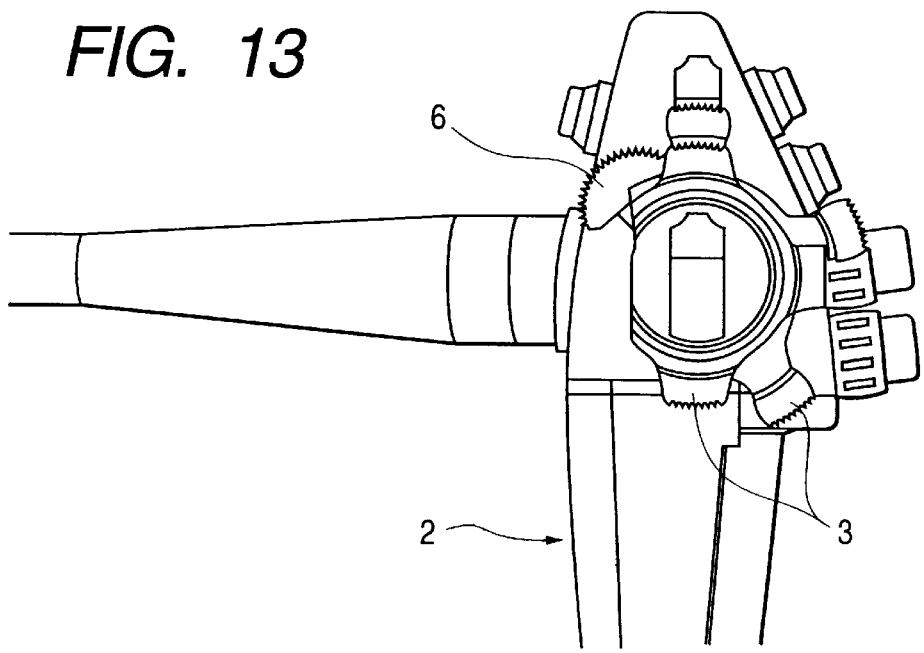
FIG. 13 is a side view showing the position of an optical system operating lever under the normal observation state.
Figure 14:
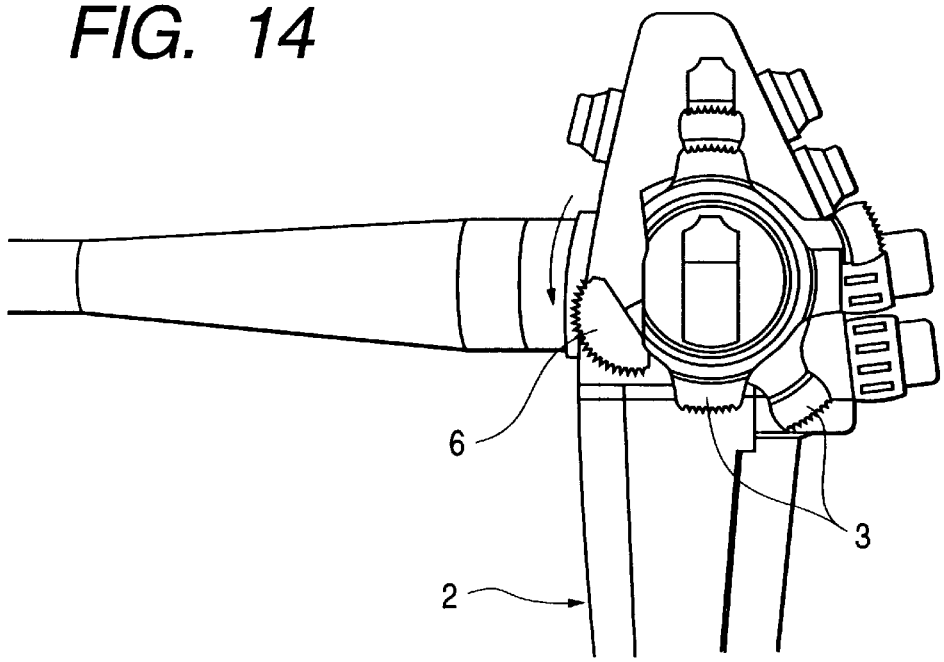
FIG. 14 is a side view showing the position of the optical system operating lever under the proximity magnification observation state.

FIGS. 13 and 14 show the movement range of the optical system operating lever 6, which is used as described above, with the bending operation knob 3 partially cut away. In particular, FIG. 13 shows the position of the lever 6 in the normal observation state, and FIG. 14 shows the position of the lever 6 in the proximity magnification observation state. The optical system operating lever 6 located at the back side of the operating unit 2 (i.e., the operator side) is movable between these two positions.

Figure 15:
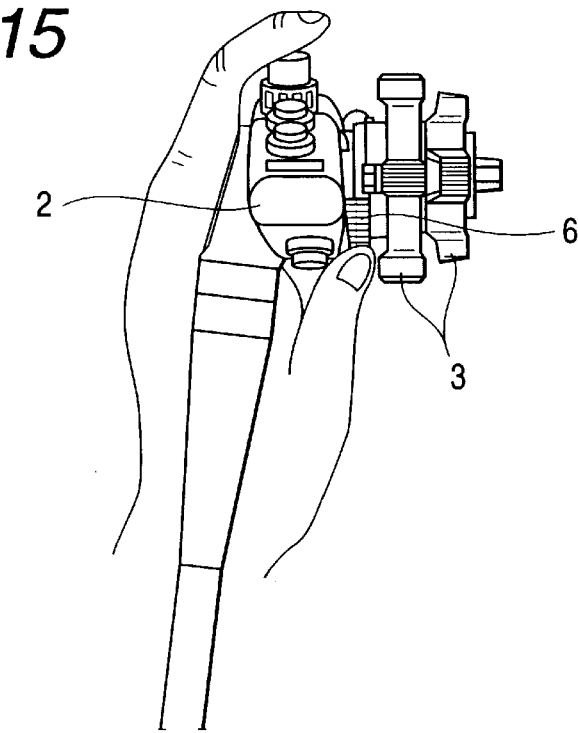
FIG. 15 is a plan view in a state where the optical system operating lever is operated by the left hand holding the operating unit.

FIG. 15 shows a state where the optical system operating lever 6 is operated, as viewed from above. The optical system operating lever 6 can be operated very easily using the thumb of the operator's left hand holding the operating unit 2.

The thumb of the operator's left hand is first used for operating the bending operation knob 3 for directing the front end of the insertion unit 1 to the diseased part. When the diseased part is captured in the observation screen, the thumb of the left hand is slightly shifted parallelly toward the operating unit 2 to operate the optical system operating lever 6. As a result, the operator can freely perform the observation magnification changing operation between the normal observation state and the proximity magnification observation state while securely holding the insertion unit 1 with his right hand.

While the invention has been specifically described herein, it will be apparent that numerous modifications may be made thereto without departing from the spirit and scope of the invention. For example, the operating unit may be configured so as to perform one of the focusing and zooming operations, or one of the objective lens group 21 and the solid state imaging device 24 may be moved by pulling the operating wire 25. Also, the optical system operating lever 6 may be configured so as to have a shape of an operating knob or an operating handle.

What is claimed is:

1. An operating unit for an endoscope, said operating unit comprising:

an optical system operating member for focusing and/or zooming operations on an observation optical system, said optical system operating member being disposed at a position such that said optical system operating member is operable by a thumb of a hand holding said operating unit; and a bending operation knob for remotely bending a bending unit formed at a front end portion of an insertion unit of the endoscope, said bending operation knob being disposed on a side face of said operating unit, and said optical system operating member is rotatable coaxially with said bending operation knob.

2. An operating unit according to claim 1, wherein said optical system operating member is disposed between a side face of said operating unit and said bending operation knob, with an end of said optical system operating member being directed toward an operator holding said operating unit.

3. An endoscope comprising:

an insertion unit;

a bending unit at a front end portion of said insertion unit;

a front end main body coupled to said bending unit;

an objective lens group and an imaging unit both installed in said front end main body and relatively movable toward and away from each other;

an operating unit coupled to a rear end portion of said insertion unit;

a bending operation member, arranged on said operating unit and rotatable about an axis, for controlling said bending unit; and an optical system operating member, arranged on said operating unit and rotatable coaxially with said bending operation member about said axis, for controlling a distance between said objective lens group and said imaging unit, said optical system operating member being operable by a thumb of a hand holding said operating unit.

4. An endoscope according to claim 3, wherein said objective lens group is movable relative to said front end main body.

5. An endoscope according to claim 3, wherein said imaging unit is movable relative to said front end main body.

6. An endoscope according to claim 3, further comprising:

a slide cylinder connected to said optical system operating member through an operating wire;

a cam cylinder coupled to said slide cylinder through a first cam groove and a first cam follower pin;

an objective lens frame supporting said objective lens group and coupled to said cam cylinder through a second cam groove and a second cam follower pin; and an imaging unit frame supporting said imaging unit and coupled to said cam cylinder through a third cam groove and a third cam follower pin.

* * * * *